US006588548B1

(12) United States Patent  
Dewitt

(10) Patent No.: US 6,588,548 B1
(45) Date of Patent: Jul. 8, 2003

(54) PHARMACY WORKSTATION AND METHOD OF OPERATION

(75) Inventor: C. Wayne Dewitt, Jacksonville, FL (US)

(73) Assignee: Load King Manufacturing, Co., Jacksonville, FL (US)

(*) Notice: Subject to any disclaimer, the term of this patent is extended or adjusted under 35 U.S.C. 154(b) by 56 days.

(21) Appl. No.: 09/721,571

(22) Filed: Nov. 22, 2000

Related U.S. Application Data

(60) Provisional application No. 60/166,982, filed on Nov. 23, 1999.

(51) Int. Cl.[7] .............................................. B65G 47/00
(52) U.S. Cl. ............................................ 186/2; 186/69
(58) Field of Search ............................... 186/2, 69, 36, 186/52, 58, 59; 312/140.1, 209, 211; 414/222.01, 675; 73/865.8, 866; 235/375, 376

(56) References Cited

U.S. PATENT DOCUMENTS

| 3,897,855 A | * | 8/1975 | Patterson .................... 186/45 |
| 4,590,866 A | | 5/1986 | Schairbaum |
| 4,755,009 A | | 7/1988 | Price et al. |
| 4,869,564 A | | 9/1989 | Lechman |
| 5,071,204 A | | 12/1991 | Price et al. |
| 5,125,727 A | | 6/1992 | Lechman et al. |
| D327,791 S | | 7/1992 | Lechman |
| D329,551 S | | 9/1992 | Lechman |
| D334,181 S | | 3/1993 | Starkey et al. |
| D335,047 S | | 4/1993 | Lechman et al. |
| 5,199,773 A | | 4/1993 | Price, Jr. et al. |
| D335,591 S | | 5/1993 | Lechman |
| D335,782 S | | 5/1993 | Lechman et al. |
| 5,208,762 A | * | 5/1993 | Charhut et al. ................ 221/9 |
| RE34,266 E | | 6/1993 | Schairbaum |
| D339,571 S | | 9/1993 | Drabczyk et al. |
| D340,229 S | | 10/1993 | Drabczyk et al. |
| D341,575 S | | 11/1993 | Drabczyk et al. |
| D342,396 S | | 12/1993 | Lechman et al. |
| 5,292,010 A | | 3/1994 | PRickles et al. |
| 5,294,193 A | | 3/1994 | Wegman et al. |
| D346,913 S | | 5/1994 | Lechman et al. |
| 5,335,605 A | | 8/1994 | Drabczyk |
| 5,346,079 A | | 9/1994 | Price, Jr. et al. |
| 5,377,951 A | | 1/1995 | Johnson et al. |
| 5,410,972 A | | 5/1995 | Schairbaum |
| D364,049 S | | 11/1995 | Lechman |
| 5,544,594 A | | 8/1996 | Schairbaum |
| 5,572,935 A | | 11/1996 | Schairbaum |
| 5,597,218 A | | 1/1997 | Lechman |

(List continued on next page.)

FOREIGN PATENT DOCUMENTS

JP 54-40484 * 3/1979 ............ B65G/1/00

Primary Examiner—Donald P. Walsh
Assistant Examiner—Mark J Beauchaine
(74) Attorney, Agent, or Firm—Allen, Dyer, Doppelt, Milbrath & Gilchrist, P.A.

(57) ABSTRACT

A pharmacy workstation includes a staging area where a prescription is initially processed by entering prescription data and customer data into a computer operable with a keyboard and recessed monitor. A prescription filling process area downstream the staging area yet proximate the keyboard includes a telephone and printer for communicating information with a doctor and insurance provider, as desired. A slot within the counter permits printed material, including prescription and customer information, and printed labels to be conveniently delivered to the process area. Gravity fed bins store empty vials and caps. A drug-filled vial, the written prescription, and the printed material are placed in a basket and conveyed downstream to a checking process area of the workstation. Once checked, the capped vial is placed in a bag, the bag sealed, and conveyed to a finished prescription holding area.

27 Claims, 9 Drawing Sheets

U.S. PATENT DOCUMENTS

| | | | |
|---|---|---|---|
| 5,597,995 A | * | 1/1997 | Williams et al. ............. 235/375 |
| 5,651,594 A | | 7/1997 | Lechman |
| 5,655,823 A | | 8/1997 | Schairbaum |
| 5,662,395 A | | 9/1997 | Lechman |
| 5,713,485 A | * | 2/1998 | Liff et al. .................... 221/129 |
| 5,720,154 A | * | 2/1998 | Lasher et al. ................. 53/168 |
| 5,740,743 A | | 4/1998 | Schairbaum |
| 5,883,370 A | * | 3/1999 | Walker et al. .............. 235/375 |
| 5,907,493 A | * | 5/1999 | Boyer et al. ................. 700/213 |
| 5,963,453 A | * | 10/1999 | East ............................ 53/493 |
| 5,964,164 A | | 10/1999 | Lechman |
| 6,019,051 A | | 2/2000 | Schairbaum |
| 6,181,979 B1 | * | 1/2001 | Murakami ................... 700/216 |
| 6,202,923 B1 | * | 3/2001 | Boyer et al. ................. 235/375 |
| 6,219,587 B1 | * | 4/2001 | Ahlin et al. ................. 700/233 |
| 6,315,720 B1 | * | 11/2001 | Williams et al. ............ 600/300 |

* cited by examiner

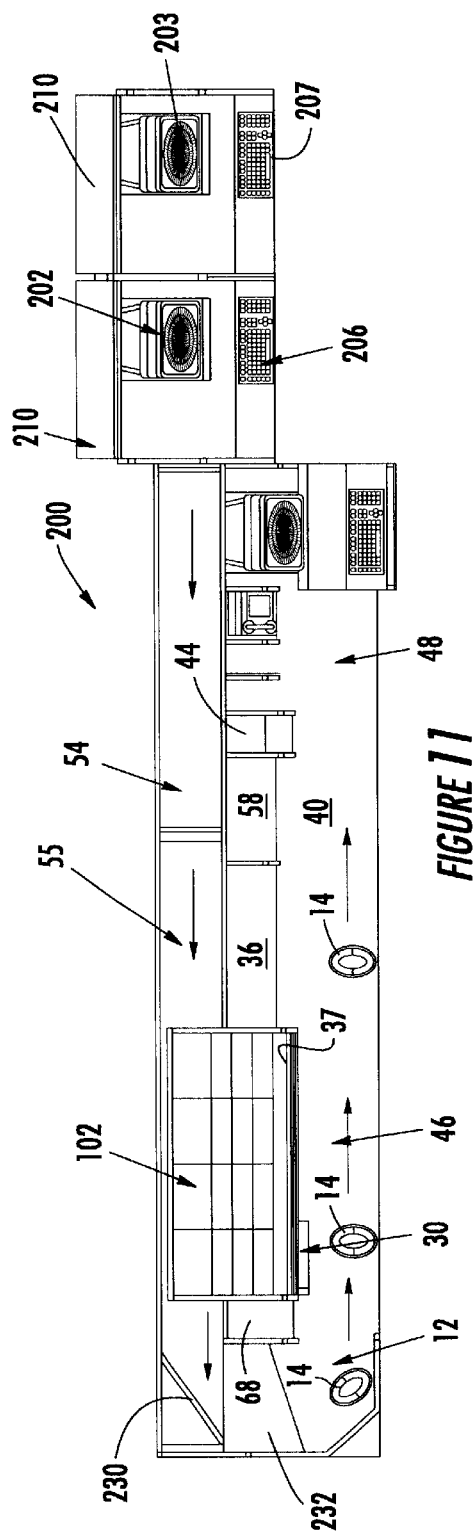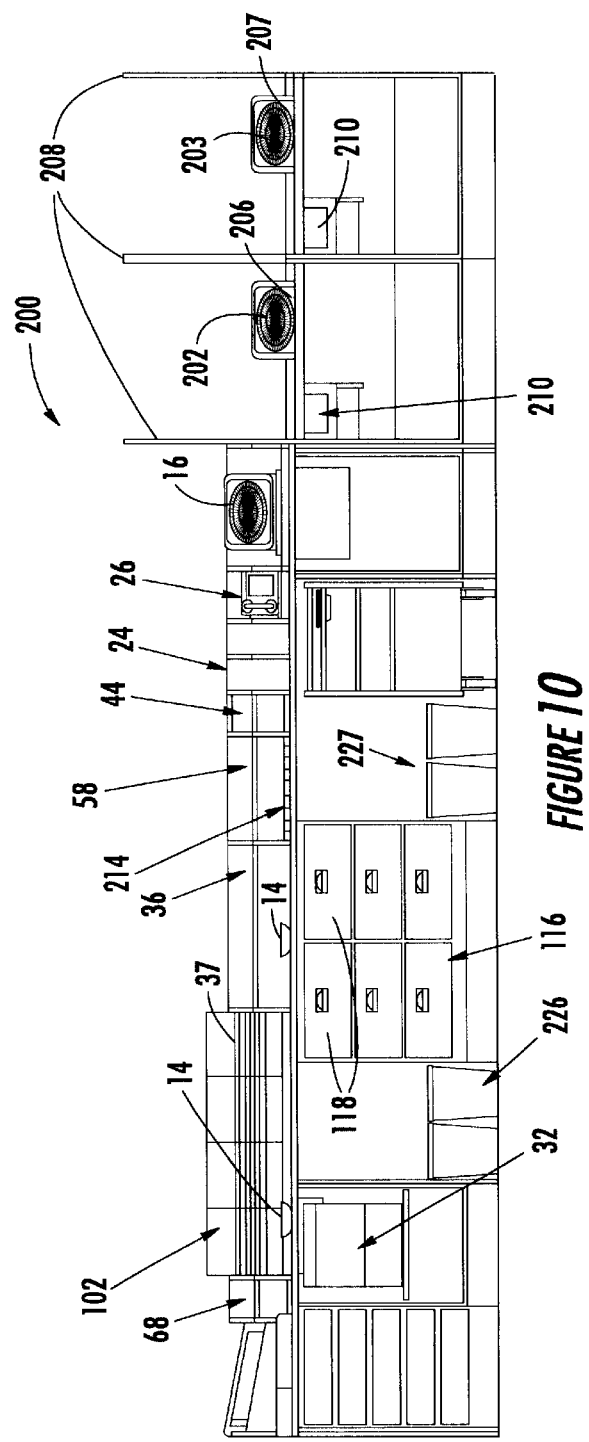

PHARMACY WORKSTATION AND METHOD OF OPERATION

CROSS REFERENCE TO RELATED APPLICATION

This application incorporates by reference and claims priority to Provisional Application Ser. No. 60/166,982 for "Pharmacy Work Center" having filing date Nov. 23, 1999 and commonly owned with the instant application.

FIELD OF THE INVENTION

The present invention relates to commercial and retail sales and service centers, and in particular to a pharmacy work center.

BACKGROUND OF THE INVENTION

One would expect any business person to agree that there is always a need to reduce costs and increase productivity. For a retail pharmacy, this cry is especially true. Based on recent statistics from the National Association of Chain Drug Stores, it is expected that prescription requests will increase by upwards of 50% within the next five years, while pharmacists will only increase by approximately 6% during this same time frame. There will be an increase of approximately 40% in the number of prescriptions per day, with a pharmacist having to fill a third more prescription than now required. To meet such anticipated demand, there is certainly a need to improve productivity in pharmacy operations through improvements in equipment and in the efficiency of working methods. There is further a need to ensure that a customer sees the store as professional, responsive to customer needs, and convenient to use.

SUMMARY OF THE INVENTION

In view of the foregoing background, it is therefore an object of the present invention to reduce cost while increasing productivity in pharmacy operations. It is further an object to provide efficient handling of prescription filling and related processing.

These and other objects, advantages and features of the present invention are provided by a method of filling a prescription, which method comprises entering prescription and customer information data into a computer using a keyboard, and printing material responsive to the information data input into the computer, wherein the printed material includes prescription preparation instructions and customer information, as well as labels. The written prescription and printed material are placed the filling area, the printed material is compared to the written prescription by a filling technician, who places the printed material and the written prescription into the basket if matching information is identified. An appropriate drug is then retrieved from a storage area. A vial is retrieved from a gravity fed dispensing bin, and filled with the drug. A cap is also retrieved from the gravity fed bin and secured to the vial. A label is then placed on the vial, which label was printed and provided with the printed material. The filled vial, an original container from which the drug was stored, and related paperwork are then placed back in the basket and moved downstream along the counter for checking. A pharmacist then compares the paper prescription to the original container from which the drugs came, compares the prescription to the drug in the vial, and checks the label on the vial. The vial is placed in a bag which is then secured shut. The bag, now a finished prescription package bag, is optionally placed in a mobile cart, and remaining paper prescription material is stored in a file area located on the counter. The now empty basket is then moved downstream for reuse.

Embodiments of the workstation include a staging area which uses a basket to contain a written prescription provided by a customer, and printed material provided by a computer printer in response to data input by a drop-off technician through keyboard data entry while viewing a recessed monitor and having access to a telephone for confirmation of data as desired. A filling area is located on a counter downstream the staging area, which filling area includes gravity fed bins holding vials and lids. Once the vials are filled with an appropriate drug, in pill form by way of example, the basket containing the filled vial, written prescription and printed material are moved further downstream to a checking area on the counter. The flow from the staging area through the filling area to the checking area may include a conveyor. Once the prescription is checked and found acceptable by a pharmacist, a sealed bag including the labeled vial is moved to a holding area, while prescription information is stored within the workstation on shelving and storage compartments. A refrigerator is provided for drug store as needed. In addition, additional shelving is provided for frequently used drugs which are pre-packaged prior to filling a prescription.

BRIEF DESCRIPTION OF THE DRAWINGS

A preferred embodiment of the invention, as well as alternate embodiments are described by way of example with reference to the accompanying drawings in which:

FIG. 10 is a front elevation view of the embodiment of FIG. 9;

FIG. 11 is a top plan view of the embodiment of FIG. 9;

DETAILED DESCRIPTION OF PREFERRED EMBODIMENTS

Figure 1:
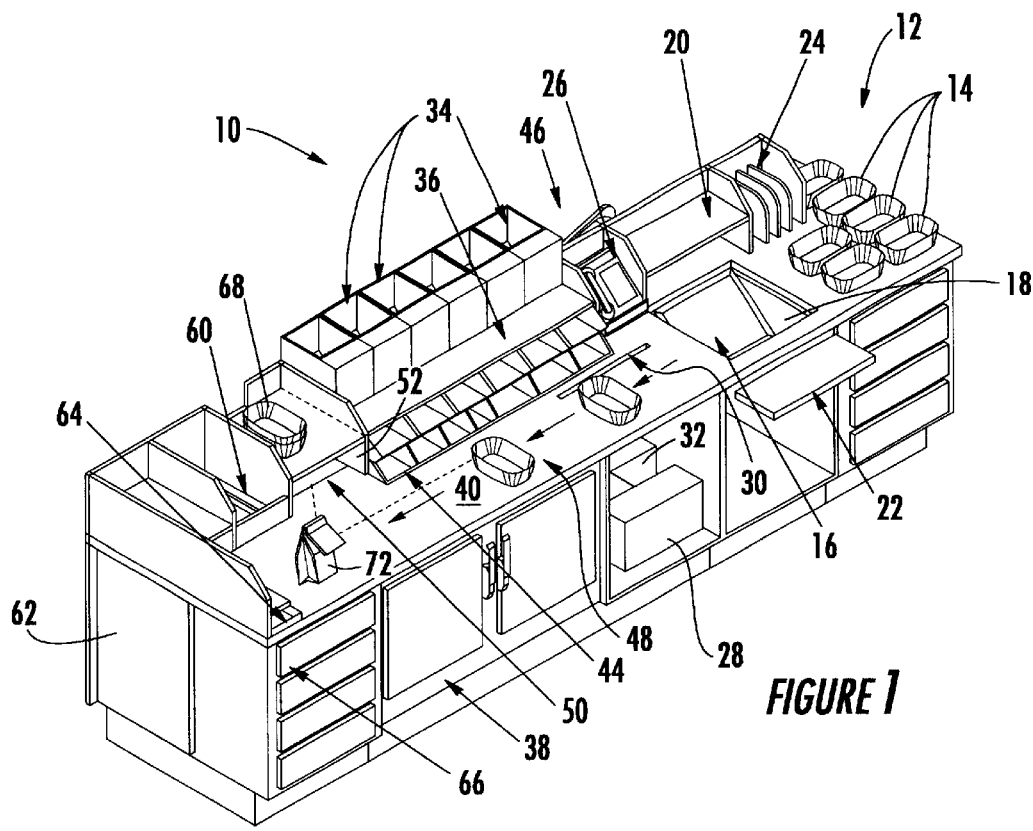
FIG. 1 is a front left perspective view of one embodiment of a pharmacy workstation of the present invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

With reference initially to FIGS. 1–4, one embodiment of the present invention comprises a pharmacy work station 10. Elements of the pharmacy workstation 10 include a staging area 12 located at one end of the workstation, which staging area is preferably a starting point of the workstation process. By way of example, baskets 14 each containing a written prescription in them are staged for processing the prescription. A monitor 16 is ergonomically positioned just to the left of the staging area 12. As illustrated with reference again to FIGS. 1–3, the monitor 16, as herein described by way of example, is carried within a recessed shelf. With the workstation 10, if it is optionally desired not to have the monitor recessed, a pre-bottled prescription shelf 20 shown by way of example, may be removed. An adjustable shelf for a keyboard 22 extends from the area of the recessed shelf 18. A storage slot 24 is located within easy reach of the computer/keyboard for storage of reference manuals, by way of example. As illustrated, the pre-bottled prescription shelf is located above the recessed monitor 18.

Figure 2:
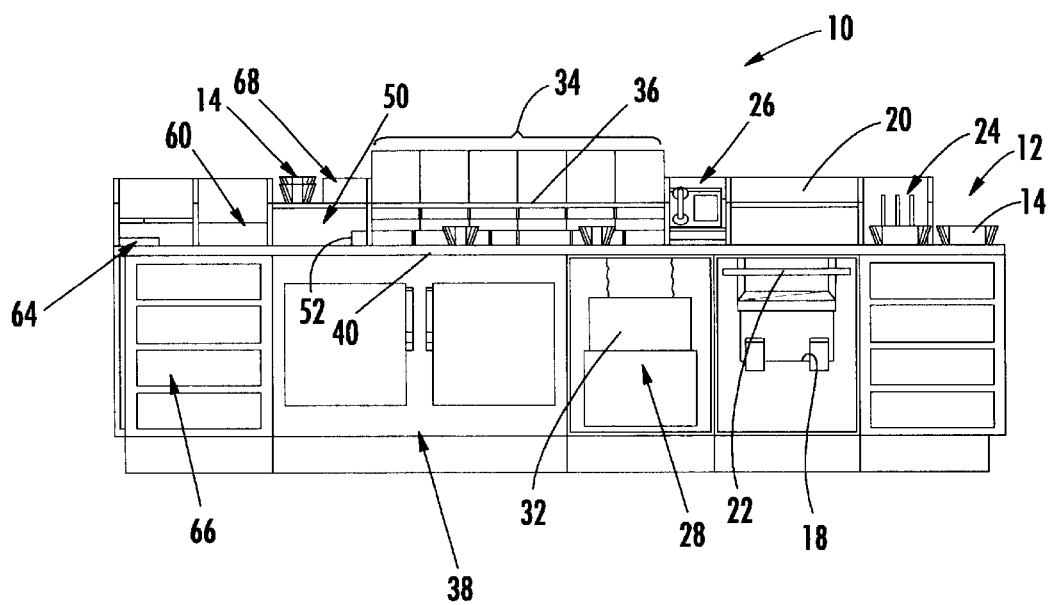
FIG. 2 is a front elevation view of the embodiment of FIG. 1
Figure 3:
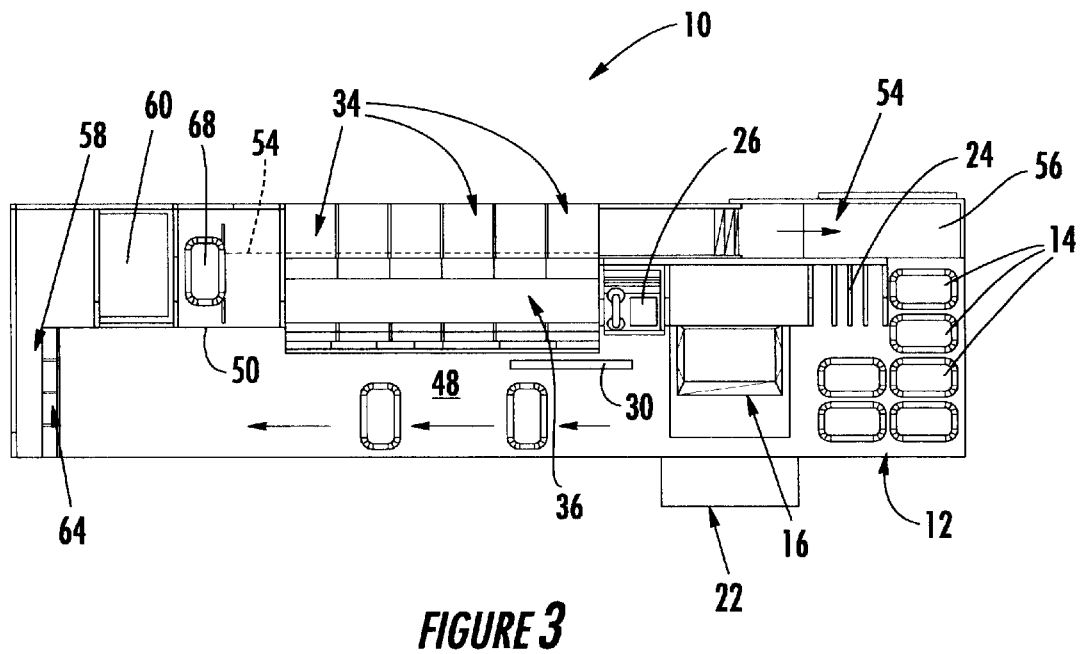
FIG. 3 is a top plan view of the embodiment of FIG. 1.

With continued reference to FIGS. 1–3, when a prescription is delivered to the staging area 12, the person working the computer identifies the prescription, and if it is a pre-bottled drug, would then pull the appropriate pre-bottle drug from the shelf 20 and places it in the basket 14. By way example, a pre-bottled drug is typically one that is a very common drug and requires a dosage that may be filled during a slow time and used at a busy time to speed up productivity by eliminating the counting and filling of the vials at the time of need. A telephone 26 is positioned within easy reach of the computer 28 and keyboard 22 to take orders over the phone and input into the computer. The computer 28 will also be used to look up information while talking with insurance companies and doctors, by way of example. A printer slot 30 is located down stream of the computer monitor 16. It is expected that a printer 32 operable with the computer will be used to print labels and customer information pertinent to the drug after relevant information is keyed into the computer 28.

With continued reference to FIGS. 1–3, gravity fed bins 34 are provided for housing different sized vials and caps, into which vials pills are poured for storage and ultimate sale. The bins 34 are located downstream of the printer slot 30. A fast mover shelf 36 is provided proximate the bins 34, and is used for the most commonly used drugs at the particular pharmacy using the workstation 10. This shelf 36 allows the pills to be picked from in front of the person filling the prescription, which saves that person from having to walk around in the pharmacy to retrieve them from a typically remote storage shelf and to return them back to a storage shelf when finished. A refrigerator 38 is located beneath a counter 40 which is used as a prescription filling area. This allows the person filling the prescription to retrieve a refrigerated drug without having to walk or turn to another area to locate a refrigerator. As illustrated with reference to FIG. 4, the height of the counter 40 is provided at an ergonomically desirable height for the person filling the prescriptions. As illustrated, the appropriate basket 14 continues downstream as the prescription is filled.

Additional storage 44 for such items as bags, is located at the end of a filling process area 46 and the beginning of a checking process area 48. By way of example, after a prescription is checked, a pharmacist will retrieve the proper sized bag, place the vial containing the pills in to the bag, and staple the bag closed with the prescription attached to the bag. Located downstream and generally across the checking process area 48 is a conveyor chute 50. By way of example, after the prescription has been packaged it is slid down the chute 50 breaking an electronic eye beam operable with a sensor 52 for communication with a conveyor 54. The conveyor 54 is shown in FIG. 3 in both dotted and solid lines. The conveyor 54 is located opposite the workstation counter 40 and runs from the conveyor chute 50 to a finished prescription holding area 56, which keeps someone from having to walk from one end of the workstation 10 to the other.

With continued reference to FIGS. 1–3, a drug return shelf 58 is located at an end of the workstation 10 opposite the staging area 12. After a prescription has been checked and packaged, the original bottle which may need to be stored at a remote location to the workstation 10 from which the drugs were taken is usually taken back to its remote storage shelf from whence it came. By way of example, during busy times, it is suggested that a temporary place for these bottles will be on the drug return shelf 58 until there is a lull in customer servicing or prescription filling activity and then multiple bottles are taken back at one time to reduce the amount of walking.

With reference again to FIG. 1, a trash chute 60 is provided for discarding, by way of example, a bottle that is empty after the prescription is checked. The bottle is A discarded into the trash chute 60, instead of being returned to the storage shelf or drug return shelf. Also, miscellaneous printed material may also be discarded that was not used in the process. A trash receptacle area 62 will house an appropriate trash can for disposal or emptying on a regular, as needed, basis. A doctor prescription bin 64 is located near the drug return shelf 58. The bin 64 includes four compartments for storing paper prescriptions after having been filled and checked. The prescriptions are divided into 4 different drug classifications, by way of example. These are stored in the bin 64 until approximately 100 prescriptions (or whichever fills the bin) and then wrapped with rubber bands and for storing in drawers 66 provided below. On occasion, prescriptions must be kept for up to five years.

A basket storage shelf 68 is provided above the conveyor chute 50. After the prescription has been checked, packaged and paper prescription filed away, the empty basket 14 is placed on the basket storage shelf 68. After a certain number of baskets have been accumulated, they are then placed down the chute to the conveyor 54, earlier described, which will convey them to the finished packaged prescription area 56 where a service person will pick them up the next time the person goes to get a finished prescription. A pill counter storage area 70 is located next to the basket storage area 68. There are usually several different methods and devices used to count pills. It is convenient to have a designated storage area for such devices. By way of further example, it may also be convenient to store a staple machine used to seal the finished package prescription in the storage area 70.

Figure 4:
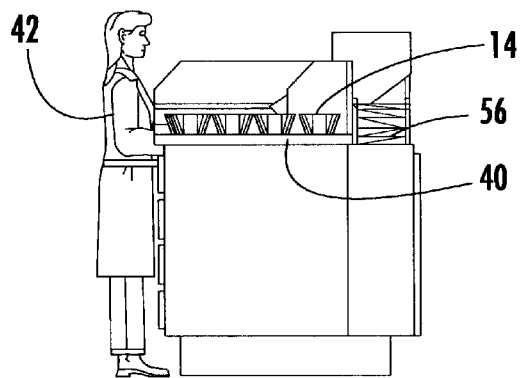
FIG. 4 is right side view of the embodiment of FIG. 1.

As above described with reference to FIGS. 3 and 4, the finished prescription holding area 56 is the area at the end of the conveyor 54. The finished packaged prescription is ready for customer pick up and here deposited for pick-up by a service person or to be filed into a will-call cabinet or the like.

In operation, the basket styled system illustrated with reference to FIGS. 1–4 may include a "Drop Off Tech"

taking the prescription from the customer, inputting the information into a computer, placing the prescription in the basket 14, turning around and placing the basket in the staging area 12 of the workstation 10. From the staging area 12 the "Pharmacist" or Filling Tech" may need to input information into the computer 28 if the "Drop Off Tech" has not done so or he may need to check information in the computer in reference to the particular customer or insurance carrier of the customer. The basket 14 is then slid down the counter 40 to the printer slot 30 in the counter. The printer 32 will print labels and other information for the customer, which is deposited through the printer slot 30 in the counter 40 to the left of the computer monitor 16. The "Filling Tech" will take the printed material and place it in the basket 14 along with the written prescription. All information associated with the order, as well as the order itself, will stay in the basket throughout the entire process to help reduce accidental mix-ups from order to order. The "Filling Tech" will then retrieve the appropriate drug from storage shelving unless it is one of the "Fast Movers" which is located on the fast mover shelf 36 formed into the gravity dispensing vial and cap bins 34. The "Filling Tech" then picks an appropriate size vial from the gravity fed bins 34, fills the prescription, picks the appropriate size cap from the gravity fed bins, and closes the vial. The "Filling Tech" then places the labels on the vial and places the finished prescription, the printed customer information, and the original bottle the drugs came from into the basket 14 and slides the basket down the counter 40 towards the checking process area 48. The "Pharmacist", seeing that there is a basket 14 in the checking process area 48 now knows that there is a prescription to be checked, then checks the prescription against the original bottle from which the drugs came, then the pills in the vial, and then the labels on the vial. The "Pharmacist" then places the original bottle from which the drugs came on the temporary drug return shelf 58, picks an appropriate size bag from the additional storage 44, places the vial into the bag, staples the printed information to the bag, sealing it shut, slides the finished packaged prescription 72 down the chute 50 triggering the sensor 52 which starts the conveyor 54. The conveyor 54 then transports the package to a holding bin at the opposite end of the counter 40 which places it in close proximity to a customer "Pick Up" area, and the finished "will call" area so that when the customer returns to pick up the prescription, the "Pick Up Tech" has the finished packaged prescription in close proximity.

Another embodiment of the present invention is illustrated with reference to FIGS. 5–8 for a workstation 100, having elements defined as described earlier with reference to FIGS. 1–4. Alternatively, and with reference to FIGS. 5–7, gravity fed vial and cap dispensing bins 102 are constructed for storage and dispensing of caps in one portion 104 and separated by one partition 106 for providing another portion 108 for vials. Another provision includes a second partition 110 for creating storage for varying caps, with one side for child proof caps and the other side for non child proof caps for a particular size vial, by way of example. Alternatively, one area may be useful for a combination cap that could operate either way depending on which end was used. Where the additional storage 44 for bags was located under the gravity fed bins 34 as described earlier with reference to FIG. 1, bag storage 112 is provided at a downstream end 114 of the bins 102, which is closer to the checking process area 48.

Figure 5:
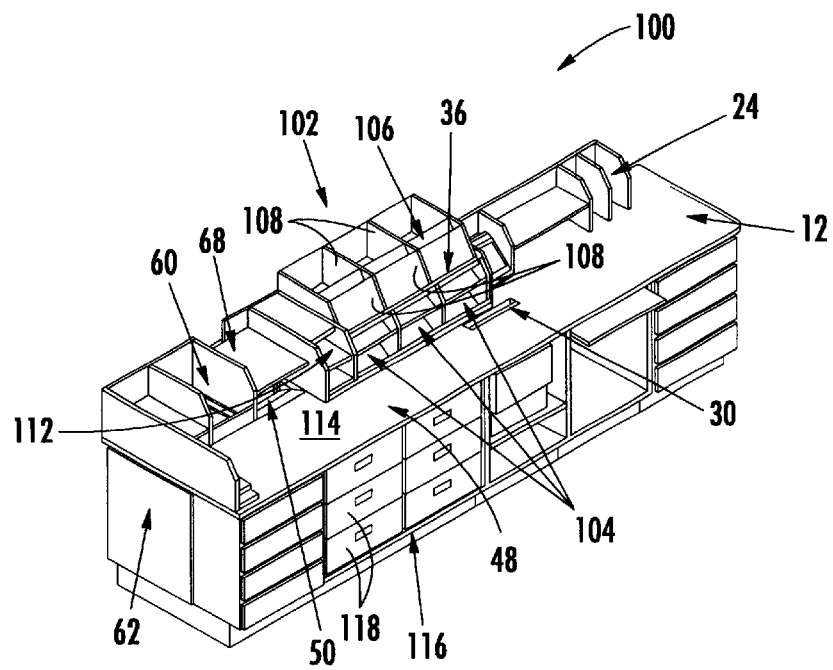
FIG. 5 is a front left perspective view of a second embodiment of a pharmacy workstation of the present invention.
Figure 6:
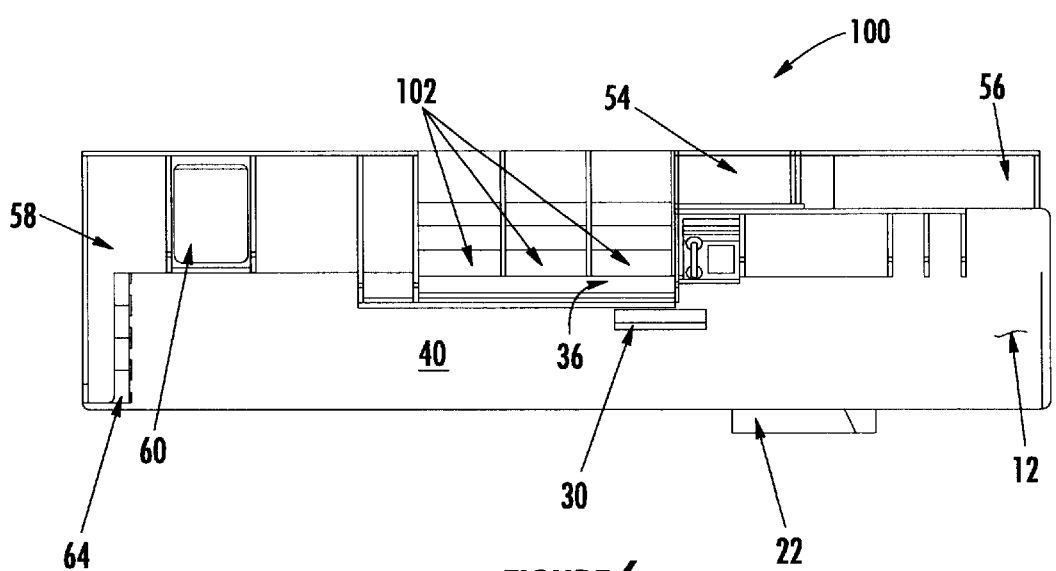
FIG. 6 is a top plan view of the embodiment of FIG. 1.
Figure 7:
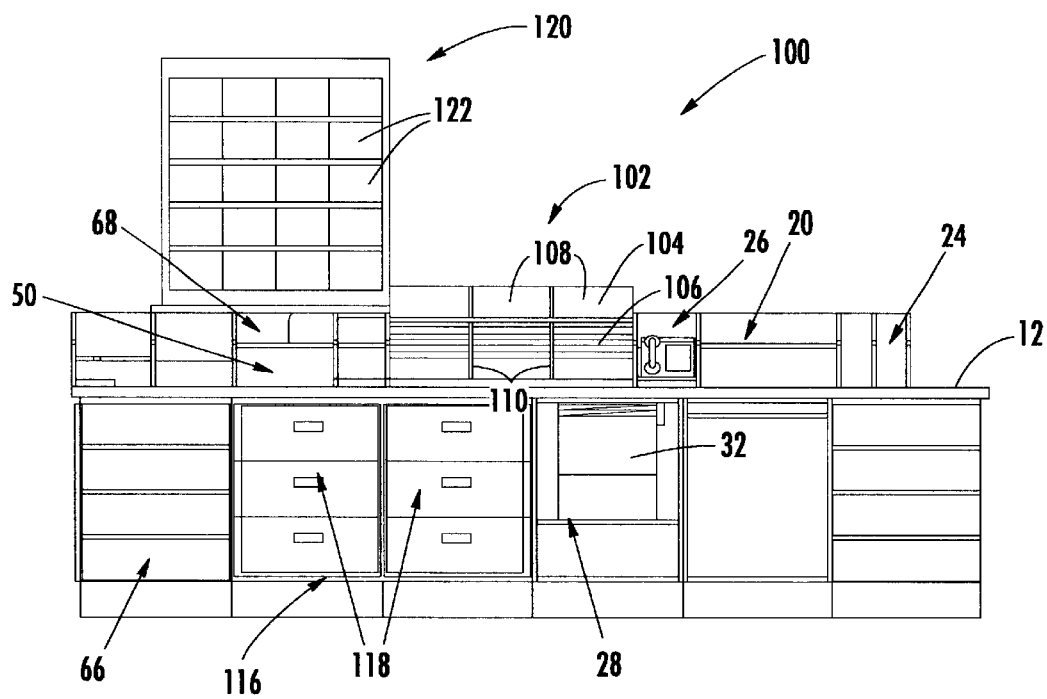
FIG. 7 is a front elevation view of the embodiment of FIG. 5, including an optional checking station.
Figure 8:
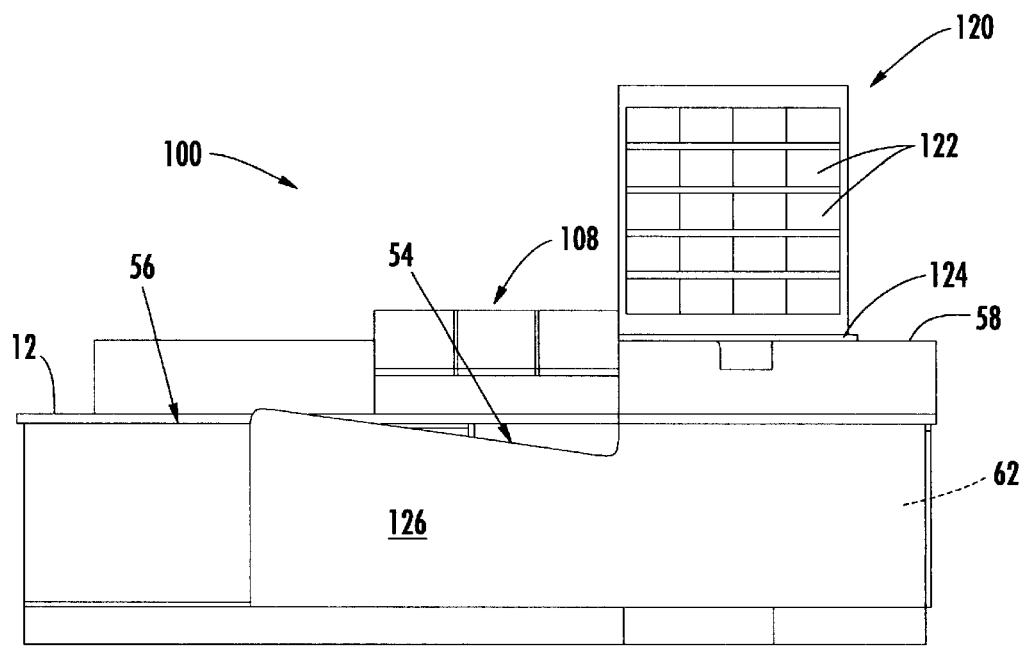
FIG. 8 is a rear elevation view of the embodiment of FIG. 7.

With continued reference to FIGS. 5–7, a drawer styled refrigerator 116 provides access to upper portions of the refrigerator without having to lean and bend. Further, separated compartments each having a drawer 118 allow for a physical separation of drugs as desired. As illustrated by way of example with reference to FIGS. 7 and 8, the workstation 100 is adapted for an optional checking station 120 that includes multiple compartments 122 carried on top of the conveyor and trash chutes 50, 60, basket shelf 68 and additional storage 44, as earlier described with reference to FIGS. 1–4. The optional checking station 120 may include a separate counter 124 perpendicular to the workstation counter 40 coming off the backside 126 behind the trash storage area 60 of the workstation 100. Such an arrangement allows access to the conveyor 54 from the backside 126 as well as through the chute 50 accessible from the front side as earlier described, which is particularly useful for a high volume pharmacy that may have a Pharmacist designated to check prescriptions, package and place package on the conveyor 54. A monitor as earlier described with reference to FIGS. 1–4, is not shown in FIGS. 5–8, and is not shown as being recessed in the drawing but could be recessed or sit on the counter, as desired.

It is to be understood that various operational functions may be located at alternate positions of a workstation depending on need. Consider yet another embodiment of the present invention, the workstation 200, as illustrated with reference to FIGS. 9–12 where earlier described functions are performed at alternate locations yet within a serial processing manner consistent with the teachings of the present invention. As earlier described with reference to the workstation 100, the workstation 200 provides alternatives depending on specific needs of a pharmacy due to its available floor space, sales volume, staff size, and the like. By way of example, and with reference now to FIGS. 9–11, a second monitor 202 is provided in a prescription drop off area 204 proximate the finished prescription holding area 56, earlier described with reference to FIGS. 3 and 6, with the staging area 12 now positioned at an opposite end of the counter as will herein be described in further detail. As desired, the second monitor 202 may be recessed for ergonomic reasons based on a compromise of a 5th percentile female 205 and a 95th percentile male in a seated position. The height and placement of the keyboard 206 uses similar criteria. Yet further, additional monitors 203 and keyboards 207 may be provided, depending on need, privacy wall 208 provide for confidentiality when dealing with customers positioned at the customer shelf 210.

Figure 9:
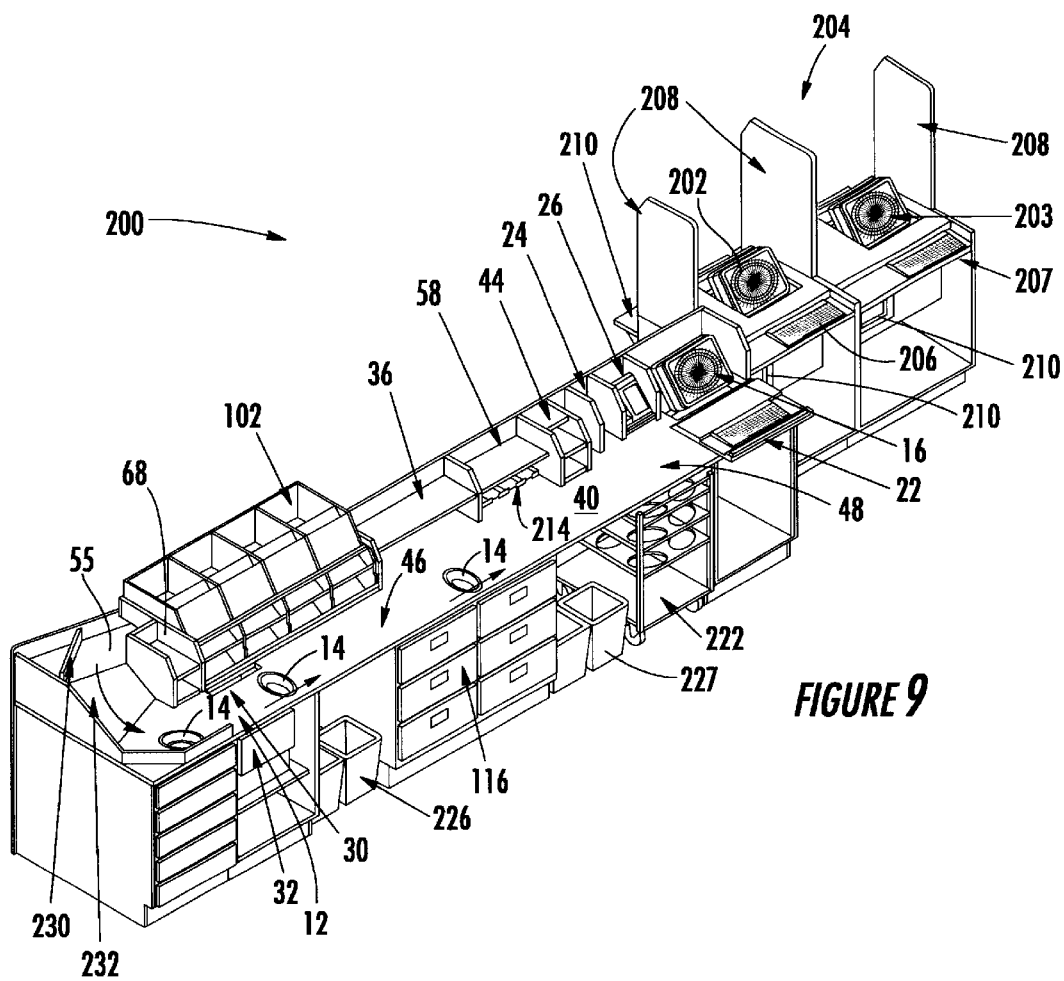
FIG. 9 is a front left perspective view of a third embodiment of a pharmacy workstation of the present invention.
Figure 12:
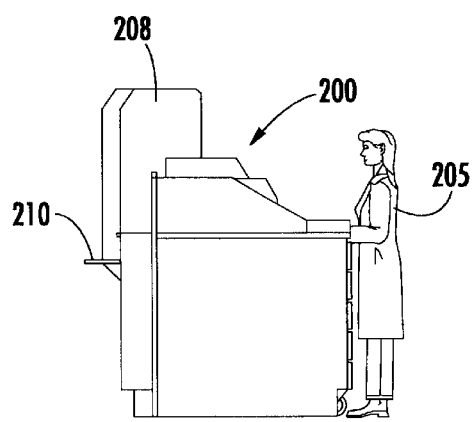
FIG. 12 is a left side view of the embodiment of FIG. 9.
Figure 13:
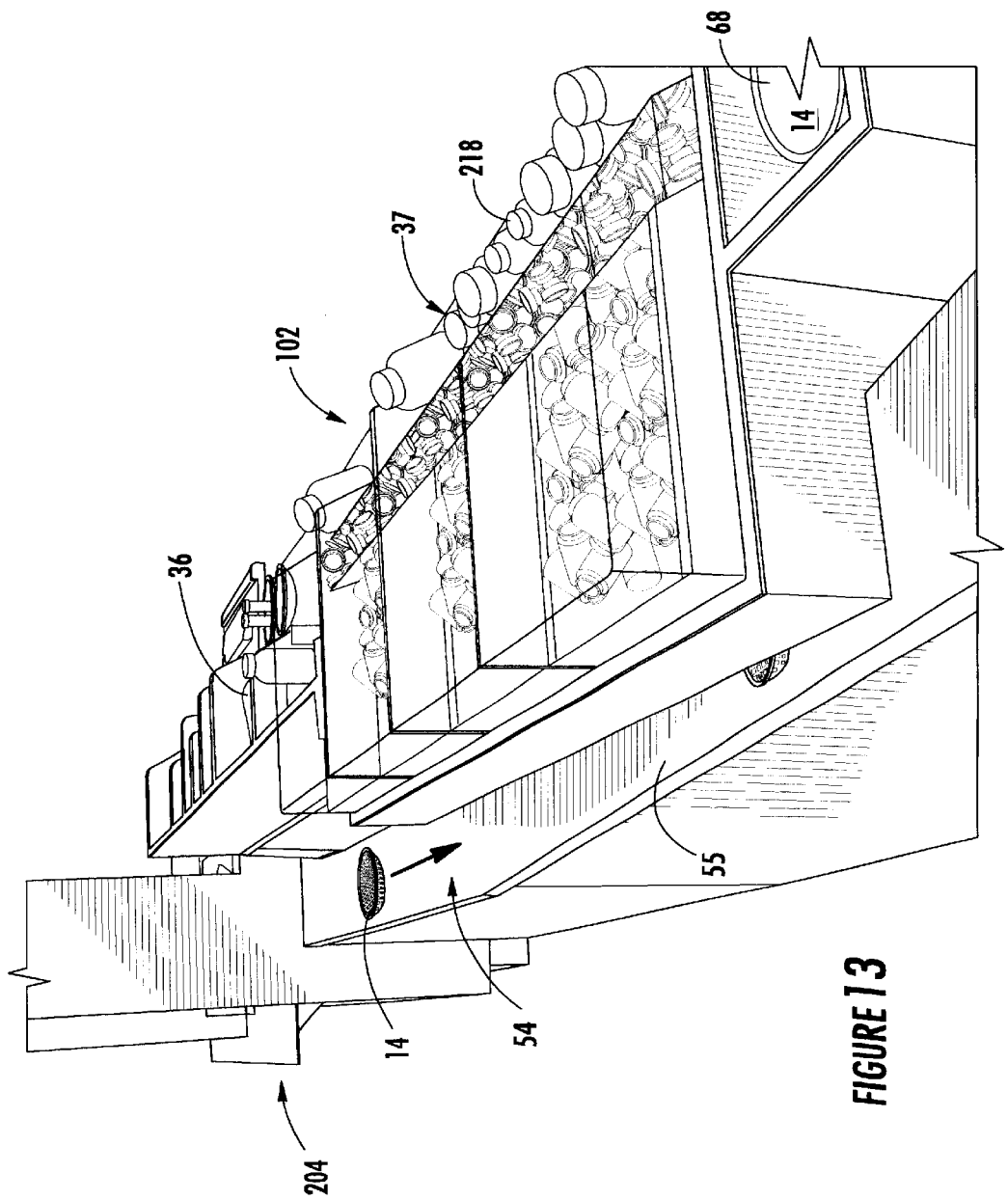
FIG. 13 is a partial rear perspective view of the workstation of FIG. 9.
Figure 14:
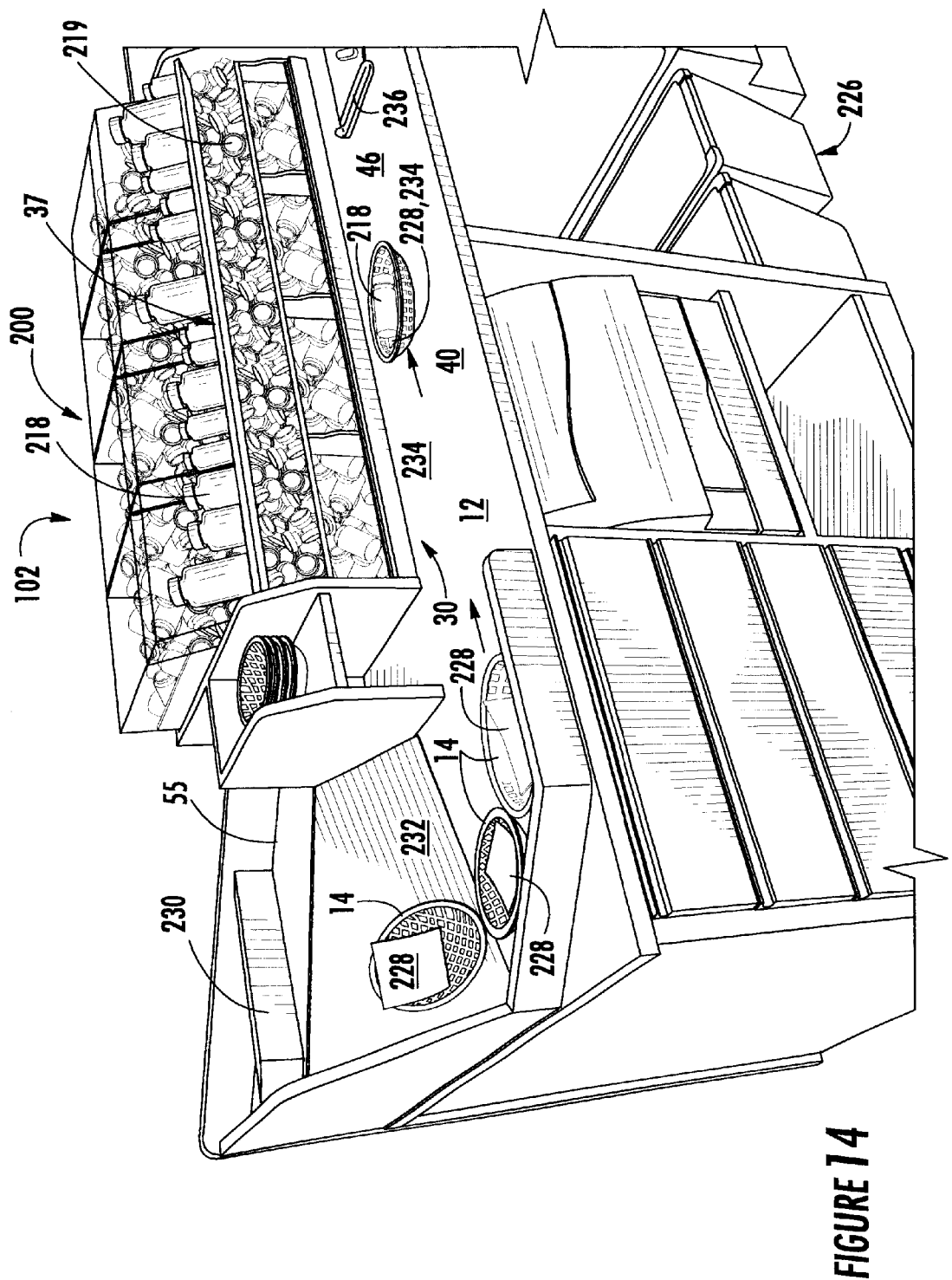
FIG. 14 is a partial left front perspective view of the embodiment of FIG. 9.

With continued reference to FIGS. 9 and 10, a basket chute 210 is positioned to the left of a "Drop Off Tech" position so that she or he does not have to adjust her position to deposit the basket into the chute 210. The conveyor 54 illustrated with reference again to FIG. 11, and to FIG. 13, eliminates the need for walking to the other end of the workstation 200, as earlier described. The basket storage shelf 68 is located as earlier described, and is within easy reach of a "Filling Tech" for use on refills which would not have a basket filled with a paper prescription from the "Drop-Off Tech". The process would start at the printed material slot 30, which as herein described for the workstation 200 is just in front and to the right of the basket shelf 68, as illustrated with reference again to FIGS. 9 and 11, and with reference to FIG. 14. The gravity fed bins 102 are as earlier described with reference to the workstation 100 and house the different size vials and caps into which the pills will be poured for sale. The bins 102 are located downstream of the printer slot 30 and are next in the filling process area 46.

As earlier described, the fast mover shelf 36 allows the pills to be picked from in front of the person filling the prescription, which saves that person from having to walk around in the pharmacy to retrieve them from a storage shelf and to return them back to a storage shelf when finished. The refrigerator 116 is located beneath the filling process area 46 of the counter 40. This allows the person filling the prescription to retrieve a refrigerated drug without having to walk or turn to another area to a refrigerator. The top drawers 118 allow access to product without having to bend down to retrieve product as occurs in a conventional refrigerator.

Figure 15:
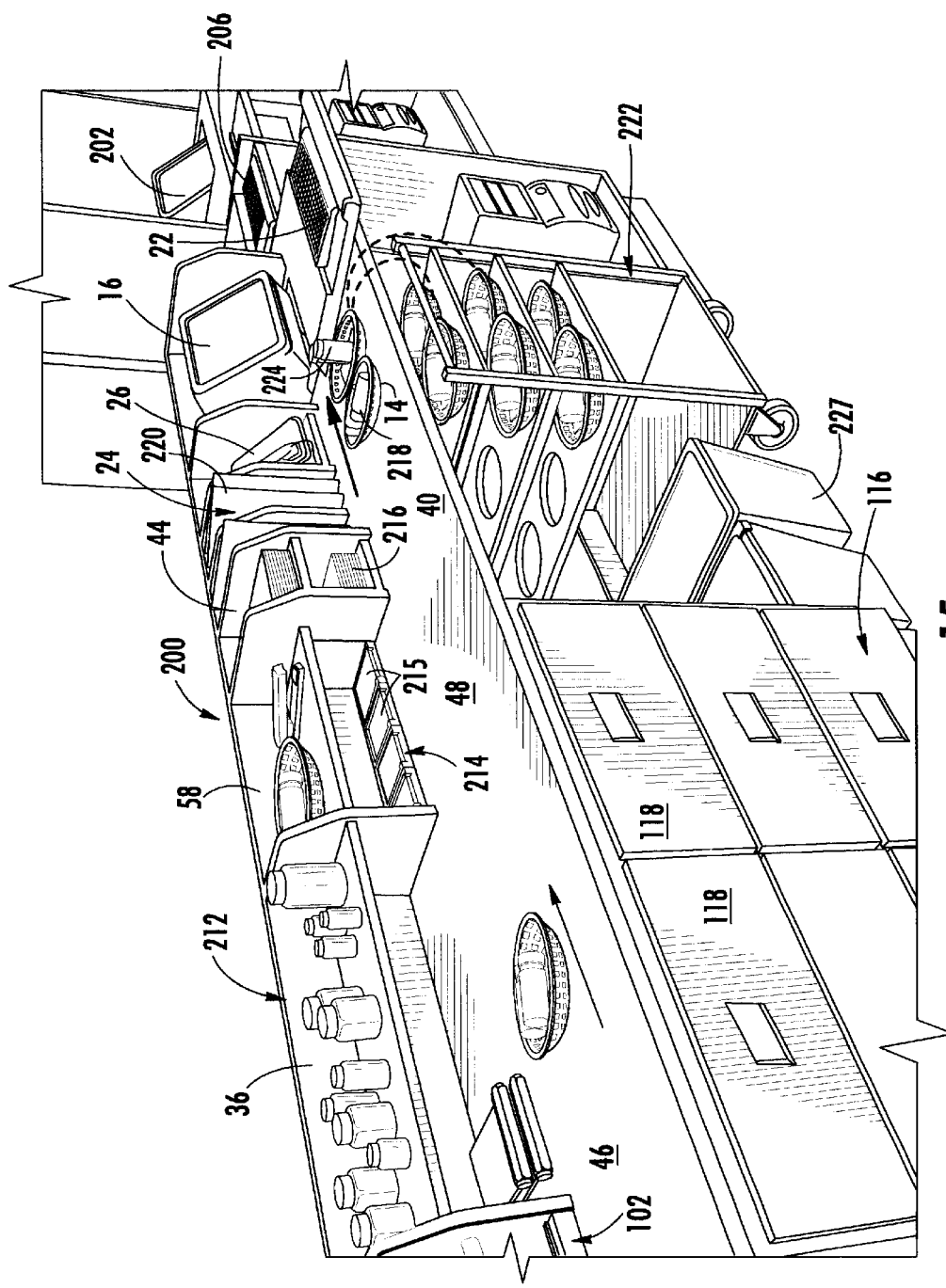
FIG. 15 is a partial medial front perspective view of the embodiment of FIG. 9.

By way of example, and with reference to FIG. 15, a pre-bottled area 212 located downstream and next to the gravity fed bins 102. By way of example, a pre- bottled drug is one that is a very common drug and dosage that may be filled during a slow time and used at a busy time to speed up productivity by eliminating the counting and filling of the vials at the time of need. The "Filling Tech" would identify the prescription and if it were determined to be a pre-bottled drug, would by-pass the gravity fed bins and go straight to this shelf to retrieve the pre-filled prescription. He or she would then put the appropriate labels on it and pass it downstream for checking.

With reference again to FIGS. 10 and 15, the drug return shelf 58 is located next to the pre-bottled area 212. A doctor prescription storage bin 214 this is located under the drug return shelf 58. This is a 4- compartment bin for storing paper prescriptions 215 after a prescription has been filled and checked. The prescriptions are divided into 4 different drug classifications. As earlier described for the workstation 100, these are stored here until there are a preselected number of prescriptions per classification and then wrapped with rubber bands and then store into the drawers below this area.

With reference again to FIGS. 9–11 and 15, the bag storage in the additional storage area 44 as earlier described, is located at the end of the checking process. After the prescription is checked, the "Pharmacist" retrieves the proper size bag 216, by way of example, places the vial 218 containing the pills in to the bag and staples the bag together to provide the finished package prescription bag 72 as earlier described with reference to FIG. 1. The reference manuals 220 are located in the storage shelf 24 within easy reach of the keyboard 22 as earlier described. The telephone 26 is within easy reach of the keyboard 22 to take orders over the telephone and input data into the computer.

With reference again to FIGS. 9, 10, and 15, a mobile cart 222 is located near the checking process area 48 so that when prescription checking is completed, the an order 224 carried within the basket 14 can be placed onto the cart 222 keeping the counter 40 free and uncluttered for continued filling and checking. Trash containers 226 are located next to the printer 32 and under the filling process area 46. Sometimes there are mistakes made that show up after inspection of the printed material. The incorrect printed material would then be thrown away and reprinted. Also, after the labels are placed on the vials, the remnants that are left are thrown away. There are also trash containers at the end of the checking station. After the prescription is checked if the original container is empty, it is then thrown away. For convenience, additional trash containers 227 are located under the counter 40 and near the checking process area 48.

In operation, and with continued reference to FIGS. 9–15, a customer approaches the drop-off area 204, and hands a paper prescription 228 to the "Drop-Off Tech". The "Tech" enters the information into the computer using the keyboard 206. The "Tech" then places the paper prescription 228 into the basket 14, and places the basket into the chute 210, which basket slides down the chute, triggers a sensor starting the conveyor 54 as the basket slides onto the conveyor. The conveyor 54 conveys the basket 14 containing the paper prescription 228 to the opposite end of the workstation 200. As herein described by way of example, the conveyor 54 includes an inclined conveyor portion 55. The basket 14 is then diverted from the conveyor 55 via a diverter 230, where it then slides down a ramp 232 onto the counter 40 next to the printer slot 30. Printed material 234 and information on the paper prescription 228 are matched and placed in the basket 14 together. The "Filling Tech" retrieves the correct drug from a storage shelf and returns to the workstation 200 where the "Tech" then counts the correct number of pills using a pill counter 236, by way of example. The "Filling Tech" then retrieves the appropriate vial 218 from the gravity fed dispensing bins 102 in front of "him" and fills the vial with the counted pills. The "Tech" then retrieves a cap 219 from the gravity fed bin in front of him and secures the cap to the vial. The "Tech" then places labels on the vial, which label were printed and provided with the printer material 234. The "Filling Tech" places the finished vial, the original container the drugs came from and related paperwork back into the basket 14 and slides the basket down the counter 40 towards the checking process area 48.

Alternatively, the "Filling Tech" may, instead of retrieving the drugs from a storage shelf, may have retrieved it from the fast mover shelf 36 or alternative located on a front fast mover shelf 37 on the gravity fed bins 102, eliminating the need to walk elsewhere. Yet alternatively, fast movers may be stored and retrieved from the refrigerator 116 located below the counter 40.

The "Pharmacist" then takes the basket 14, compares the paper prescription 228 to the original container from which the drugs came, then compares it to the pills in the vial 218, and checks all labels. The "Pharmacist" then places the original drug container on the temporary drug return shelf 58 located in front of him or her. The "Pharmacist" then retrieves a bag 216 from in front of him to the right and places the vial 218 inside, retrieves a stapler 240, by way of example, from the shelf 58 and staples pertinent customer printed material 234 to the bag, sealing it shut, then places the bag, now the finished prescription package bag 72, earlier described, in the mobile cart 222, and places the remaining paper prescription into the written prescription file or doctor bin 214 located in front of him. He then slides the empty basket 14 downstream toward the keyboard 22 so that the person working the keyboard can periodically hand the baskets to the "Drop-Off Tech".

As earlier described, the "Pharmacist" working the computer is able to take prescriptions over the telephone located in front and to the left of the monitor. He also has access to reference manuals also in front and to the left of the monitor. The finished packaged prescriptions in the mobile cart are then taken to a will-call cabinet or lazy-susan by a "Tech," by way of example. Alternatively, after the "Pharmacist" checks the prescription, instead of packaging the order, he places the basket containing the entire order in a special designed mobile cart that a "Tech" would file and package.

By way of further example, consider what may constitute an efficient workstation as including the following partial list: a minimum movement required to complete tasks; minimized reach distances; little or no bending required; specific positions for all equipment and supplies; work has directional flow; work is intuitively organized; operations are automated where practical; and anthropometric factors are optimized. Further, consider a pharmacy and an operation required, as illustrated with reference to Table 1 describing steps from the time a customer drops off a prescription to the time a clerk tenders the transaction. To appreciate more fully the benefits resulting from the present invention, compare the clerk pick-up workflow typical in the art as illustrated with reference to Table 2, with that of the present invention as illustrated with reference to Table 3. It has been estimated that over 400 hours per year are saved by use of the apparatus and methods of the present invention herein described. For yet a further appreciation of the present invention, compare the workflow of a clerk filing. The typical clerk filing workflow is illustrated with reference to Table 4, and that of the present invention is described with reference to Table 5. It has been estimated that more than 300 hours per year are saved by use of the present invention. In addition to the improved efficiency, the cost savings can well be appreciated.

TABLE 1

Workflow
Consider a typical pharmacy operation that may
include the following procedures:

1. Drop-off Tech receives paper Rx from customer
2. Drop-off Tech inputs info into computer
3. Labels, warnings, etc. printed on printer
4. Drop-off Tech places paper Rx on counter
5. Filling Tech combines printed material and paper Rx with a close pin
6. Filling Tech retrieves drug from shelving
7. Filling Tech fills Rx
8. Filling Tech puts appropriate labels on vial
9. Filling Tech slides paper Rx, printed material and vial containing Rx down the countertop
10. Pharmacist checks Rx
11. Pharmacist slides printed material and vial containing Rx down the countertop
12. Pharmacist places paper Rx in 1 of 4 containers on the countertop according to classification, for storage
13. Pharmacist returns unused portion of bottled drug back to the shelving
14. Clerk takes checked Rx
15. Clerk Places the individual vials in individual slots in the Will Call cabinet
16. Clerk Writes the corresponding slot number on the prescription paperwork
17. Clerk files the paperwork by customer name in a separate customer file
18. Customer approaches clerk for pick-up
19. Clerk looks up customer name in file
20. Clerk removes all Rx's from file
21. Clerk uses number on individual file to locate corresponding numbered slot
22. Clerk retrieves individual vial from individual slot - (this is repeated for every Rx in the file for that customer)
23. Customer is asked to confirm the number of Rx's
24. If the number matches, the Clerk then packages the Rx's
25. If the number does not match - Clerk looks for an incomplete job in the filing process (work in process) and proceeds to have it filled or informs the customer of a problem with that particular Rx
26. Clerk tenders the transaction

TABLE 2

Clerk Pick-up Workflow
Current Pick-up Procedure for One Order with Two Prescriptions 1. Customer approaches clerk for pick-up
2. Customer says he is here to pick up prescription for R. J. Soward
3. Clerk walks 63" to the file
4. Clerk reaches for the "S" file
5. Clerk thumbs through the "S" files until she identifies the name Soward
6. Clerk identifies all the R. J. Soward TABLE 2-continued Clerk Pick-up Workflow
Current Pick-up Procedure for One Order with Two Prescriptions 7. Clerk lifts all of the R. J. Soward files out of the files
8. Clerk walks 33" to the will call cabinet
9. Clerk identifies a number written on a R. J. Soward file
10. Clerk identifies which drawer that number should be in
11. Clerk opens the drawer (may bend down, reach up, or not depending on location of drawer)
12. Clerk identifies that number with a particular slot within the drawer
13. Clerk reaches for the vial
14. Clerk retrieves the vial from the slot
15. Clerk compares the vial to the paperwork for accuracy
16. Clerk closes drawer
17. Clerk identifies a number written on a R. J. Soward file
18. Clerk identifies which drawer that number should be in
19. Clerk opens the drawer (may bend down, reach up, or not depending on location of drawer)
20. Clerk identifies tat number with a particular slot within the drawer
21. Clerk reaches for the vial
22. Clerk retrieves the vial from the slot
23. Clerk compares the vial to the paperwork for accuracy
24. Clerk closes drawer
25. Clerk walks 45" to the customer
26. Clerk places the vial and paperwork on the counter
27. Clerk asks customer to confirm how many prescriptions there are supposed to be
28. If the number matches,
29. Clerk then locates the bags
30. Clerk reaches for bag
31. Opens the bag
32. Places the vial inside
33. Locates paperwork
34. Locates stapler
35. Staples paperwork to bag
36. Clerk presses correct buttons on register
37. Identifies cost
38. Clerk informs customer of cost
39. Clerk reaches for money or check (customer may use debit card at machine instead)
40. Puts money, etc. in register
41. Makes change (if applicable)
42. Closes register
43. Hands customer money
44. Hands customer receipt
45. Hands customer packaged prescription

TABLE 3

Clerk Pick-up Workflow
Invention Pick-up Procedure for One Order with
Two Prescriptions (443 hrs/yr saved)

1. Customer approaches clerk for pick-up
2. Customer says he is here to pick up prescription for Jimmy Smith
3. Clerk walks 69" to lazy susan
4. Clerk spins lazy susan to the "S" bay
5. Clerk looks throught th "S" packages until she sees Smith
6. Clerk reaches for the packages with Jimmy Smith on them
7. Lifts packages out of bin
8. Clerk looks through the "8" packages until she sees Smith
9. Clerk reaches for the packages with Jimmy Smith on them
10. Lifts packages out of bin
11. Clerk walks to the customer 69"
12. Customer is asked to confirm the number of Rx's
13. If the number matches,
14. Clerk presses the correct buttons on register
15. Identifies cost
16. Clerk informs customer of cost
17. Clerk reaches for money or check (customer may use debit card at machine instead)
18. Puts money, etc. in register
19. Makes change (if applicable)
20. Closes register TABLE 3-continued Clerk Pick-up Workflow
Invention Pick-up Procedure for One Order with
Two Prescriptions (443 hrs/yr saved)

21. Hands customer money
21. Hands customer receipt
22. Hands customer packaged prescription

TABLE 4

Clerk Filing Workflow
Current Procedure for 5 Orders

1. Clerk walks 96" from the cashier area to the checked area
2. Clerk locates a checked order on the countertop
3. Clerk reaches for the vials and the paperwork for one order
4. Clerk lifts the vials with one hand and the paperwork with the other
5. Clerk walks to the Will Call cabinet 95"
6. Clerk opens a drawer (may bend, reach up, or not depending which drawer is opened)
7. Clerk places the individual vials in individual slots in the Will Call cabinet
8. Clerk identifies the number written on the slot
9. Clerk writes the corresponding slot number on the prescription paperwork
10. Clerk closes drawer
11. Clerk walks to the file area 33"
12. Clerk identifies the name on the paperwork
13. Clerk searches the file for that name
14. Clerk places the paperwork in the file according to proper alphabetical order
15. Clerk walks 67" back to the checked area
16. Clerk locates a checked order on the countertop
17. Clerk reaches for the vials and the paperwork for one order
18. Clerk lifts the vials with one hand and the paperwork with the other
19. Clerk walks to the Will Call cabinet 95"
20. Clerk opens a drawer (may bend, reach up, or not depending which drawer is opened)
21. Clerk places the individual vials in individual slots in the Will Call cabinet
22. Clerk identifies the number written on the slot
23. Clerk Writes the corresponding slot number on the prescription paperwork
24. Clerk closes drawer
25. Clerk walks to the file area 33"
26. Clerk identifies the name on the paperwork
27. Clerk searches the file for that name
28. Clerk Places the paperwork in the file according to proper alphabetical order
29. Clerk walks 67" back to the checked area
30. Clerk locates a checked order on the countertop
31. Clerk reaches for the vials and the paperwork for one order
32. Clerk lifts the vials with one hand and the paperwork in the other
33. Clerk walks to the Will Call cabinet 95"
34. Clerk opens a drawer (may bend, reach up, or not depending which drawer is opened)
35. Clerk places the individual vials in individual slots in the Will Call cabinet
36. Clerk identifies the number written on the slot
37. Clerk Writes the corresponding slot number on the prescription paperwork
38. Clerk closes drawer
39. Clerk walks to the file area 33"
40. Clerk identifies the name on the paperwork
41. Clerk searches the file for that name
42. Clerk Places the paperwork in the file according to proper alphabetical order
43. Clerk walks 67" back to the checked area
44. Clerk locates a checked order on the countertop
45. Clerk reaches for the vials and the paperwork for one order
46. Clerk lifts the vials with one hand and the paperwork with the other
47. Clerk walks to the Will Call cabinet 95"
48. Clerk opens a drawer (may bend, reach up, or not depending on which drawer is opened)
49. Clerk places the individual vials in individual slots in the Will Call cabinet TABLE 4-continued Clerk Filing Workflow
Current Procedure for 5 Orders 50. Clerk identifies the number written on the slot
51. Clerk Writes the corresponding slot number on the prescription paperwork
52. Clerk closes drawer
53. Clerk walks to the file area 33"
54. Clerk identifies the name on the paperwork
55. Clerk searches the file for that name
56. Clerk Places the paperwork in the file according to proper alphabetical order
57. Clerk walks 67" back to the checked area
58. Clerk locates a checked order on the countertop
59. Clerk reaches for the vials and paperwork for one order
60. Clerk lifts the vials with one hand and the paperwork with the other
61. Clerk walks to the Will Call cabinet 95"
62. Clerk opens a drawer (may bend, reach up, or not depending on which drawer is opened)
63. Clerk places the individual vials in individual slots in the Will Call cabinet
64. Clerk identifies the number written on the slot
65. Clerk Writes the corresponding slot number on the prescription paperwork
66. Clerk closes drawer
67. Clerk walks to the file area 33"
68. Clerk identifies the name on the paperwork
69. Clerk searches the file for that name
70. Clerk places the paperwork in the file according to proper alphabetical order
71. Clerk walks 63" back to the cashier area

TABLE 5

Clerk Filing Workflow
Invention Procedure for 5 Orders (319 hrs/yr saved)

1. Clerk walks 145" from the cashier area to the checked area
2. Clerk pulls cart out from under the countentop
   (cart may already be out if Pharmacist is in the checking mode)
3. Clerk reaches for packages (5 packages)
4. Clerk lifts the group of packages
5. Clerk walks 75" to the lazy susan
6. Clerk identifies the name on a package
7. Spins the lazy susan to the appropriate bin
8. Reaches for that package
9. Places that package in the appropriate bin
10. Clerk identifies the name on a package
11. Spins the lazy susan to the appropriate bin
12. Reaches for that package
13. Places that package In the appropriate bin
14. Clerk identifies the name on a package
15. Spins the lazy susan to the appropriate bin
16. Reaches for that package
17. Places that package in the appropriate bin
18. Clerk identifies the name on a package
19. Spins the lazy susan to the appropriate bin
20. Reaches for that package
21. Places that package in the appropriate bin
22. Clerk identifies the name on a package
23. Spins the lazy susan to the appropriate bin
24. Reaches for that package
25. Places that package in the appropriate bin
26. Clerk walks 70" back to the cashier area It is to be understood that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

That which is claimed is:

1. A method of filling a prescription, the method comprising:

receiving a written prescription from a customer by a service representative located at one end of a workstation;

entering prescription and customer information data into a computer using a keyboard by the service representative, the keyboard located proximate the one end of the workstation;

placing the written prescription into a basket by the service representative who places the basket into a chute for guiding the basket onto a conveyor;

conveying the basket containing the written prescription to a staging area of the workstation;

electronically printing material responsive to the information data input into the computer, the printed material including prescription preparation instructions and customer information;

comparing the printed material to the written prescription by a filling technician;

placing the printed material and the written prescription into the basket by the filling technician if matching information is identified;

retrieving a drug carried in a container from a storage area;

retrieving a vial from a gravity fed dispensing bin;

filling the vial with at least a portion of the drug;

retrieving a cap from the gravity fed bin and securing the cap to the vial for providing a finished vial;

placing a label on the vial, which label was printed and provided with the printed material;

placing the finished vial, the container from which the drug was stored, and related paperwork including the printed material and the written prescription into the basket and moving the basket downstream towards a checking process area;

comparing the written prescription to the container from which the drug was retrieved, by a pharmacist, which pharmacist then compares the written prescription to the drug in the vial, and checking the label on the vial;

placing the container on a drug return shelf;

retrieving a bag by the pharmacist and placing the vial in the bag, sealing the bag shut;

placing the bag, now a finished prescription package bag, in a mobile cart;

placing any remaining paper prescription into a written prescription file located at the workstation; and moving the now empty basket downstream for reuse by the service representative.

2. A method of filling a prescription, the method comprising:

placing a written prescription into a basket by a service representative;

conveying the basket containing the written prescription to a staging area of a workstation;

electronically printing material responsive to information data input into a computer, the printed material including prescription preparation instructions, a label, and customer information;

providing the printed material at the staging area;

comparing the printed material to the written prescription;

placing the printed material into the basket with the written prescription if matching information relating the written prescription to the printed material is identified;

retrieving a drug appropriate for filling the written prescription;

filling a vial with the drug;

placing the vial having the drug therein into the basket with the printed material and the written prescription; and moving the basket downstream towards a checking process area.

3. A method according to claim 2, further comprising:

receiving the written prescription from a customer by a service representative located at one end of the workstation; and entering prescription and customer information data into the computer by the service representative.

4. A method according to claim 2, wherein comparing the printed material to the written prescription is performed by a filling technician.

5. A method according to claim 2, further comprising retrieving a drug from a storage area; and retrieving a vial.

6. A method according to claim 2, further comprising:

a retrieving a cap;

securing the cap to the vial for providing a finished vial; and placing the label on the vial.

7. A method according to claim 2, further comprising comparing the written prescription to the drug retrieved, by a pharmacist, which pharmacist then compares the written prescription to the drug in the vial, and checks the label on the vial.

8. A method according to claim 2, further comprising:

providing a container having the drug therein for the retrieving thereof;

placing the container on a drug return shelf.

9. A method according to claim 2, further comprising:

retrieving a bag by the pharmacist and placing the vial in the bag, sealing the bag closed; and placing the closed bag, now a finished prescription package bag, in a mobile cart.

10. A method according to claim 9, further comprising placing any remaining paper prescription into a written prescription file.

11. A method according to claim 2, further comprising:

providing a gravity fed dispensing bin carried by the workstation for storing a plurality of vials therein; and retrieving the vial from the gravity fed dispensing bin.

12. A method according to claim 11, further comprising providing a shelf proximate the gravity fed dispensing bin for storing commonly used drugs thereon.

13. A method according to claim 2, further comprising providing a refrigerator proximate the staging area for storing refrigerated drugs therein, and wherein the drug retrieving includes retrieving the drug from the refrigerator.

14. A method of filling a prescription, the method comprising:

receiving a written prescription from a customer located at one end of a workstation;

conveying the written prescription to a staging area of the workstation;

electronically printing material responsive to information data input into a computer, the printed material including prescription preparation instructions, a label, and customer information;

delivering the printed material to the staging area through a slot carried within a work surface thereof;

further conveying the printed material and the written prescription if matching information is identified;

retrieving a drug from a storage area;

filling a vial with at least a portion of the drug;

conveying the vial containing the portion of the drug, any remaining drug, the printed material, and the written prescription downstream along the workstation towards a checking process area;

comparing the written prescription to the drug retrieved; and comparing the written prescription to the drug in the vial.

15. A method according to claim 14, further comprising:

entering prescription and customer information data into the computer using a keyboard by a service representative, the keyboard located proximate the one end of the workstation; and placing the written prescription into a basket by the service representative for moving the basket downstream the workstation.

16. A method according to claim 14, wherein comparing the printed material to the written prescription is performed by a filling technician.

17. A method according to claim 14, further comprising:

providing a gravity fed dispensing bin at the workstation; and retrieving a vial from the gravity fed dispensing bin.

18. A method according to claim 17, further comprising:

retrieving a cap from the gravity fed dispensing bins securing the cap to the vial for providing a finished vial; and placing the label on the finished vial, which label was printed and provided with the printed material.

19. A method according to claim 14, placing the remaining drug onto a drug return shelf.

20. A method according to claim 14, further comprising:

placing the vial in the bag;

sealing the bag shut; and placing the bag, now a finished prescription package bag, in a mobile cart for delivery to a customer.

21. A method according to claim 17, further comprising providing a shelf proximate the gravity fed dispensing bin for storing commonly used drugs thereon.

22. A method of filling a prescription, the method comprising:

receiving a written prescription from a customer by a service representative located at one end of a workstation;

placing the written prescription into a basket by the service representative for conveying the basket downstream;

conveying the basket containing the written prescription downstream to a staging area of the workstation;

providing printed material including prescription preparation instructions and customer information;

comparing the printed material to the written prescription;

placing the printed material and the written prescription into the basket if matching information is identified.

23. A method according to claim 22, further comprising the service representative entering prescription and customer information data into a computer using a keyboard located proximate the one end of the workstation.

24. A method according to claim further comprising:

retrieving a drug carried in a container from a storage area;

retrieving a vial from a gravity fed dispensing bin carried by the workstation;

filling the vial with at least a portion of the drug;

retrieving a cap from the gravity fed bin and securing the cap to the vial for providing a finished vial;

placing a label on the vial, which label was printed and provided with the printed material;

placing the finished vial, the container from which the drug was stored, the printed material, and the written prescription into the basket and moving the basket; and moving the basket downstream towards a checking process area of the workstation.

25. A method according to claim 23, further comprising:

comparing the written prescription to the container from which the drug was retrieved, by a pharmacist, which pharmacist then compares the prescription to the drug in the vial, and checks the label on the vial; and placing the original drug container on a drug return shelf.

26. A method according to claim 25, further comprising:

retrieving a bag by the pharmacist and placing the vial in the bag, sealing the bag shut; and placing the bag, now a finished prescription package bag, in a mobile cart for delivery to the customer.

27. A method according to claim 24, further comprising providing a shelf proximate the gravity fed dispensing bin for storing commonly used drugs thereon.

* * * * *